`US005512597A`

United States Patent [19]
Kyba et al.

[11] Patent Number: 5,512,597
[45] Date of Patent: Apr. 30, 1996

[54] POLYMERIC QUATERNARY AMMONIUM COMPOUNDS AND THEIR USE AS OPHTHALMIC ANTIMICROBIALS

[75] Inventors: Evan P. Kyba; Joon S. Park, both of Arlington, Tex.

[73] Assignee: Alcon Laboratories, Inc., Fort Worth, Tex.

[21] Appl. No.: 372,696

[22] Filed: Jan. 13, 1995

Related U.S. Application Data

[63] Continuation of Ser. No. 126,354, Sep. 24, 1993, abandoned, which is a continuation-in-part of Ser. No. 790,319, Nov. 8, 1991, abandoned.

[51] Int. Cl.$^6$ ................................................. A61K 31/14
[52] U.S. Cl. ...................... 514/642; 424/78.04; 528/397; 514/912; 564/291; 564/292
[58] Field of Search .................... 528/397; 424/78.04; 564/291, 292; 514/642, 912

[56] References Cited

U.S. PATENT DOCUMENTS

| | | | |
|---|---|---|---|
| 3,874,870 | 4/1975 | Green et al. | 71/67 |
| 3,931,319 | 1/1976 | Green et al. | 260/567.6 P |
| 4,001,432 | 1/1977 | Green et al. | 424/329 |
| 4,012,446 | 3/1977 | Green et al. | 260/567.6 P |
| 4,025,653 | 5/1977 | Green et al. | 514/325 |
| 4,027,020 | 5/1977 | Green et al. | 424/248.56 |
| 4,089,977 | 5/1978 | Green et al. | 514/642 |
| 4,407,791 | 10/1983 | Stark | 424/80 |
| 4,444,750 | 4/1984 | Green et al. | 514/642 |
| 4,525,346 | 6/1985 | Stark | 424/80 |
| 5,037,647 | 8/1991 | Chowhan et al. | 424/78 |

FOREIGN PATENT DOCUMENTS 536017 8/1941 United Kingdom.

*Primary Examiner*—Peter O'Sullivan
*Attorney, Agent, or Firm*—Sally Yeager

[57] ABSTRACT

The invention relates to polymeric quaternary ammonium compounds which are useful as disinfectants and/or preservatives in ophthalmic compositions.

13 Claims, No Drawings

POLYMERIC QUATERNARY AMMONIUM COMPOUNDS AND THEIR USE AS OPHTHALMIC ANTIMICROBIALS

This application is a continuation of application Ser. No. 08/126,354, filed Sep. 24, 1993 now abandoned; which is a continuation-in-part of Ser. No. 07/790,319, filed Nov. 8, 1991 now abandoned.

This is a continuation-in-part of U.S. Patent Application Serial No. 07/790,319 filed Nov. 8, 1991.

BACKGROUND OF THE INVENTION

The present invention relates generally to a class of antimicrobials useful in pharmaceutical and cosmetic products. In particular, the present invention relates to polymeric quaternary ammonium compounds which are useful as disinfectants and preservatives for ophthalmic, pharmaceutical and contact lens care products.

Polymeric quaternary ammonium compounds as a class have been known for many years. British Patent No. 536,017 (Aug. 30, 1941), assigned to E. I. DuPont de Nemours (the "DuPont Patent"), discloses linear polymeric quaternary ammonium compounds and methods for their preparation. The method of the DuPont Patent may be generically described as a condensation reaction between a lower alkyl dihalide and a difunctional ditertiary amine. Contemplated uses for the compounds of the DuPont Patent include their use in photographic processing, to treat leather, as mold inhibitors and pesticides, and as modifying agents. There is no mention of use of these compounds as disinfectants or preservatives in pharmaceutical products.

U.S. Pat. Nos. 3,931,319 (Jan. 6, 1976), 4,001,432 (Jan. 4, 1977) and 4,012,446 (Mar. 15, 1977), all issued to Green, et al., disclose a group of high molecular weight "capped" linear polymeric quaternary ammonium compounds found to be effective microbiocides (antimicrobials). The Green, et al. compounds are "capped" in the sense that both ends of the chains terminate in quaternary ammonium moieties. In a continuation-in-part application, now U.S. Pat. No. 4,027,020 (May 31, 1977), Green, et al. disclose a process for making randomly capped linear polymeric quaternary ammonium compounds; that is, the polymers produced by the improved process include those with very short chain lengths as well as those having relatively long chain lengths. These compounds were also found to have antimicrobial activity.

U.S. Pat. Nos. 4,407,791 (Oct. 4, 1983) and 4,525,346 (Jun. 25, 1985), both issued to Stark, disclose improved disinfecting solutions for contact lenses, wherein the aqueous solutions contain the Green, et al. polymers including the commercially known Onamer M®. In addition, U.S. Pat. No. 5,037,647 (Aug. 6, 1991 ), issued to Chowhan et al., disclose aqueous antimicrobial ophthalmic solutions containing Onamer M® in combination with an anionic complexing agent to prevent or to reduce binding of the polymer to contact lenses.

SUMMARY OF THE INVENTION

For purposes of this specification, disinfectants and/or preservatives shall be collectively referred to as "antimicrobials" and compounds having disinfecting and/or preserving efficacy shall be referred to as compounds having "antimicrobial activity." In addition, the terms "polymeric quaternary ammonium compounds" or "polymers" shall hereinafter refer to polymeric quaternary ammonium compounds and their pharmaceutically acceptable salts, and the terms shall be used interchangeably throughout this specification.

It has now been found that certain polymeric quaternary ammonium compounds, of generic relationship to those disclosed in the DuPont Patent and the Green, et al. patents, are particularly suitable for use in ophthalmic compositions as antimicrobials. However, the polymers of the present invention are unique in at least two respects: 1 ) it has been discovered that optimum performance for the indicated utility is achieved only for a narrow range of molecular size, i.e., length of the polymer; and 2) the polymers of the present invention are characterized by a terminal end group R, which is —N(CH$_3$)$_2$, While applicants are bound by no theory, it appears that the polymer length and end capping function of the polymers of the present invention limit corneal toxicity, absorption and adsorption to contact lenses and maximize biocidal activity under the product designs and uses disclosed herein.

The ophthalmic compositions of the present invention comprise the polymers of the present invention. These compositions include: contact lens care products, such as chemical disinfecting and storage solutions and preserved saline solutions; and other types of ophthalmic compositions, such as artificial tears and topical pharmaceutical preparations.

DETAILED DESCRIPTION OF THE INVENTION

Preferred polymers of the present invention are those of Structure (I), below:

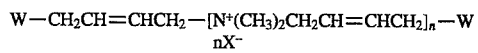

wherein:

W=N(CH$_3$)$_2$ or OH;

X is a pharmaceutically acceptable anion, preferably a halide, particularly chloride; and n is an integer from 16 to 32, preferably from 20 to 24.

The polymers of the present invention can be made and purified by utilizing the methods of the DuPont Patent or the Green, et al. patents to synthesize a polymeric mixture, then to separate the desired molecular weight fraction by chromatographic methods, by using dialysis membranes, by trituration, by a combination of these methods or by some other means.

The polymers of the present invention may be used as antimicrobials in ophthalmic compositions, particularly as disinfectants in contact lens care products and as preservatives in other types of ophthalmic compositions, such as artificial tears or topical pharmaceutical preparations. In general, the polymers of the present invention will be present in the compositions at a concentration between about 0.00001 and 1.0 percent by weight (wt%). If used as a disinfectant, the polymers are preferably present at a concentration of between about 0.0005 and 0.5 wt %; if use as a preservative, the polymers are present at a concentration between about 0.00005 and 0.05 wt %. It is preferred that the polymers are present at a concentration of between 0.001 and 0.05 wt % if used as a disinfectant and between 0.0001 and 0.01 wt % if used as a preservative.

The ophthalmic compositions of the present invention may additionally contain other components, for example, ophthalmically acceptable buffers, tonicity agents, surfactants and therapeutic agents.

EXAMPLE 1

1,4-Dichloro-2-butene (1.88 grams (g) 0.015 moles (mol)) was added dropwise to 2.13 g (0.015 mol) of N,N,N',N'-tetramethyl-2-butene-1,4-diamine in 50 milliliters of isopropanol. This reaction mixture was reacted for three hours with stirring under reflux conditions. High molecular weight polymer was found to be precipitated at room temperature. This reaction mixture was treated with 50 ml of aqueous 40% weight/volume N,N-dimethylamine, reacted at 50° C. for one hour in a pressure reactor, then precipitated out with 200 ml of acetone. This precipitate was triturated with isopropanol, ethanol, methanol at room temperature. The white precipitate was collected and dried in vacuo. Nuclear magnetic resonance spectrum and other analysis methods confirmed the structure of the above polymer. A number average molecular weight was also estimated by NMR.

EXAMPLE 2

Utilizing the same synthetic and purification procedure as described in Example 1, using 1.69 g(0.0135 mol) of 1,4-dichloro-2-butene and 2.13 g (0.015 mol) of N,N,N',N'-tetramethyl-2-butene-1,4-diamine, a white polymer was obtained.

EXAMPLE 3

1,4-Dichloro-2-butene (12.5 g, 0.1 mol) was added dropwise to 14.23 g (0.1 mol) of N,N,N',N'-tetramethyl-2-butene-1,4-diamine in 150 ml of water at room temperature for a period of 30 minutes. This reaction mixture was reached at 50°– 55° C. for two hours with stirring, transferred to a pressure bottle, and treated with 50 ml of aqueous 40% N,N-dimethylamine. This was reacted at 50° C. for one hour and precipitated with 500 ml of acetone. By following the procedure described above in example 1, a white polymeric material was obtained and analyzed.

EXAMPLE 4

The procedure described in the synthesis of Example 1 was employed using 2.16 g (0.017 mol.) of 1,4-dichloro-2-butene and 2.46 g (0.017 mol.) of N,N,N',N'-tetramethyl-2-butene-1,4-diamine, except that the reaction was performed in 20 ml of dimethylformamide at room temperature. The reaction mixture was raised to 50° C. and stirred for one hour. A white precipitate was formed. This mixture was treated with 5.0 g of an aqueous solution of dimethylamine (40% w/v) and heated at 45° C. for 40 minutes. Following the purification process described above in Example 1, a white precipitate was obtained. Nuclear magnetic resonance spectrum and elemental analysis confirmed the structure of the polymer. A number average molecular weight was also estimated by NMR.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of disinfecting a contact lens, comprising contacting a contact lens with a composition comprising an ophthalmically acceptable vehicle and a disinfecting amount of a substantially pure form of a polymeric quaternary ammonium compound of structure:

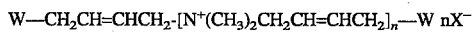

wherein:

$W=N(CH_3)_2$;

X is a pharmaceutically acceptable anion; and n is an integer from 16 to 32.

2. The method of claim 1, wherein n is an integer from 20 to 24.

3. The method of claim 1, wherein X is a halide.

4. The method of claim 3, wherein X is chloride.

5. The method of claim 1, wherein the polymeric quaternary ammonium compound is present at a concentration between about 0.00001 and about 1.0 percent by weight.

6. The method of claim 5, wherein the polymeric quaternary ammonium compound is present at a concentration between about 0.0005 and about 0.5 percent by weight.

7. The method of claim 6, wherein the polymeric quaternary ammonium compound is present at a concentration between about 0.001 and about 0.05 percent by weight.

8. An ophthalmic composition comprising an ophthalmically acceptable vehicle and a disinfecting amount of a substantially pure form of a polymeric quaternary ammonium compound of structure:

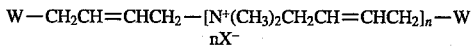

wherein:

$W=N(CH_3)_2$;

X is a pharmaceutically acceptable anion; and n is an integer from 16 to 32.

9. The ophthalmic composition of claim 8, wherein the polymeric quaternary ammonium compound is present at a concentration between about 0.00001 and about 1.0 percent by weight.

10. The ophthalmic composition of claim 9, wherein the polymeric quaternary ammonium compound is present at a concentration between about 0.0005 and about 0.5 percent by weight.

11. The ophthalmic composition of claim 9, wherein the polymeric quaternary ammonium compound is present at a concentration between about 0.0005 and about 0.5 percent by weight.

12. The ophthalmic composition of claim 11, wherein the polymeric quaternary ammonium compound is present at a concentration between about 0.001 and about 0.05 percent by weight.

13. The ophthalmic composition of claim 11, wherein the polymeric quaternary ammonium compound is present at a concentration between about 0.0001 and about 0.01 percent by weight.

* * * * *